US007704705B2

(12) United States Patent
Bornscheuer et al.

(10) Patent No.: US 7,704,705 B2
(45) Date of Patent: Apr. 27, 2010

(54) ESTERASES AND THEIR USE FOR PROCESSES FOR KINETIC RESOLUTION OF BUTINOLESTERS

(75) Inventors: Uwe T. Bornscheuer, Greifswald (DE); Marlen Schmidt, Greifswald (DE); Markus Kaehler, Hamburg (DE); Andre Rieks, Hamburg (DE)

(73) Assignee: BASF SE (DE)

( * ) Notice: Subject to any disclaimer, the term of this patent is extended or adjusted under 35 U.S.C. 154(b) by 9 days.

(21) Appl. No.: 12/083,301

(22) PCT Filed: Oct. 5, 2006

(86) PCT No.: PCT/EP2006/067056

§ 371 (c)(1),
(2), (4) Date: Apr. 8, 2008

(87) PCT Pub. No.: WO2007/042444

PCT Pub. Date: Apr. 19, 2007

(65) Prior Publication Data

US 2009/0155865 A1 Jun. 18, 2009

(30) Foreign Application Priority Data

Oct. 10, 2005 (EP) .................................. 05109395

(51) Int. Cl.
*C12Q 1/44* (2006.01)
*C12N 9/16* (2006.01)
*C12N 9/18* (2006.01)
(52) U.S. Cl. .......................... 435/19; 435/196; 435/197
(58) Field of Classification Search ................... 435/19, 435/196, 197
See application file for complete search history.

(56) References Cited

U.S. PATENT DOCUMENTS

| 7,384,787 B2 * | 6/2008 | Kazlauskas et al. ......... 435/440 |
| 2004/0219625 A1 | 11/2004 | Bornscheuer et al. |
| 2005/0181472 A1 | 8/2005 | Hauer et al. |

FOREIGN PATENT DOCUMENTS

| DE | 10042892 A1 | 3/2002 |
| WO | WO-02/094949 A2 | 11/2002 |

OTHER PUBLICATIONS

Baumann, M., et al., "Rapid Screening of Hydrolases for the Enantioselective Conversion of 'Difficult-to-Resolve' Substrates", Tetrahedron, 2000, vol. 11, Issue 23, pp. 4781-4790.
Park, S., et al., "Focusing Mutations into the *P. fluorescens* Esterase Binding Site Increases Enantioselectivity More Effectively than Distant Mutations", Chemistry & Biology, 2005, vol. 12, pp. 45-54.
Cheeseman, J. D., et al., "Structure of an Aryl Esterase from *Pseudomonas fluorescens*", Acta Cryst., 2004, vol. 60, Issue 7, pp. 1237-1243.
Cheeseman, J. D., Abstract of Papers American Chemical Society, 2004, col. 60, vol. 228, Issue 1, pp. 189-190.
Horsman, G. P., et al., "Mutations in Distant Residues Moderately Increase the Enantioselectivity of *Pseudomonas fluorescens* esterase towards Methyl 3-Bromo-2-methylpropanoate and Ethyl 3-Phenylbutyrate", Chem, Eur. J., 2003, vol. 9, pp. 1933-1939.
Henke, E., et al., "Directed Evolution of an Esterase from *Pseudomonas fluorescens*. Random Mutagenesis by Error-Pron PCR or a Mutator Strain and Identification of Mutants Showing Enhanced Enantioselectivity by a Resorufin-Based Fluorescence Assay", Biol. Chem., 1999, vol. 380, pp. 1029-1033.
Schmidt, M., et al., "Directed Evolution of an Esterase from *Pseudomonas fluorescens* Yields a Mutant with Excellent Enantioselectivity and Activity for the Kinetic Resolution of a Chiral Building Block", ChemBioChem, 2006, vol. 7, pp. 805-809.
Reetz, M. T., et al., "Erzeugung Enantioselektiver Biokatalysatoren fuer die Organische Chemie durch In-Vitro-Evolution", Angew. Chem., 1997, vol. 109, No. 24, pp. 2961-2963.
Reetz, M. T., et al:, "Creation of Enantioselective Biocatalysts for Organic Chemistry by In Vitro Evolution", Angew, Chem. Int. Ed. Engl., 1997, vol. 36, No. 24, pp. 2830-2832.
Liebeton, K., et al., "Directed Evolution of an Enantioselective Lipase", Chem. Biol., 2000, vol. 7, pp. 709-718.
Reetz, M. T., et al., "Directed Evolution of Selective Enzymes and Hybrid Catalysts", Tetrahedron, 2002, vol. 58, pp. 6595-6602.
Gallagher, W. P., et al., "PMHS-Mediated Couplings of Alkynes or Benzothiazoles with Various Electrophiles: Application to the Synthesis of (−)- Akolactone A", J. Org. Chem., 2003, vol. 68, pp. 6775-6779.
Ko, H., et al., "Total Synthesis of Pancratistatin Relying on the [3,3]-Sigmatropic Reaarangement", J. Org. Chem., 2004, vol. 69, pp. 112-121.
Molander, G. A., et al., "Synthesis and Application of Chiral Cyclopropane-Based Ligands in Palladium-Catalyzed Allylic Alkylation", J. Org. Chem, 2004, vol. 69, pp. 8062-8069.
Fu, X., et al., "Improved Large-Scale Synthesis of (R)- Benzyl 4-Hydroxyl-2-pentynoate from (R)-3-Butyn-2-ol", Organic Process research & Development, 2002, vol. 6, pp. 308-310.
Pietruszka, J., et al., "New 1,3-Disubstituted Enantiomerically Pure Allylboronic Esters by Johnson Rearrangement of Boron-Substituted Allyl Alcohols", Eur, J. Org. Chem., 2004, vol. 24, pp. 5011-5019.
Horvath, A., et al., "Enantiocontrolled Synthesis of 3-Pyrrolines from α-Amino Allenes", Eur. J. Org. Chem., 2004, vol. 15, pp. 3240-3243.
Yanada, R., et al., "Indium-Mediated Atom-transfer and Reductive Radical Cyclizations of Iodoalkynes: Synthesis and Biological Evaluation of HIV-Protease Inhibitors", J. Org. Chem., 2004, vol. 69, pp. 2417-2422.

(Continued)

*Primary Examiner*—Tekchand Saidha
(74) *Attorney, Agent, or Firm*—Connolly Bove Lodge & Hutz LLP

(57) ABSTRACT

New enzymes having esterase activity and their use for processes for kinetic resolution of butinolesters.

11 Claims, No Drawings

OTHER PUBLICATIONS

Hartner, F. W., et al., "Method for the Synthesis of 5,6,7,8-Tetrahydro-1,8-naphthyridine Fragments for αvβ$_3$ Integrin Antagonists", J. Org. Chem., 2004, vol. 69, pp. 8723-8730.

Yoshida, M., et al., "Palladium-Catalyzed Carbon Dioxide Elimination-Fixation reaction of 4-Methoxycarbonyloxy-2-buten-1-ols", J. Org. Chem., 2004, vol. 69, pp. 1590-1597.

Krebsfaenger, N., et al., "Characterization and Enantioselectivity of a Recombinant Esterase from *Pseudomonas fluorescens*", enzyme and Microbial Technology, 1998, vol. 22, pp. 641-646.

Nakamura, K., et al., "The Effect of Catechin Derivatives on the Enantioselectivity of Lipase-Catalyzed Hydrolyses of Alkynol Benzoate esters", Tetrahedron:*Asymmetry*, 2002, vol. 13, pp. 415-422.

Schubert, T., et al., "Enantioselective Synthesis of Both Enantiomers of Various Propargylic Alcohols by Use of Two Oxidoreductases", Eur. J. Org. Chem., 2001, vol. 22, pp. 4181-4187.

"ESTE_PSEFL", Database UniProtKB, Accession Database P22862, Aug. 1, 1991.

* cited by examiner

ESTERASES AND THEIR USE FOR PROCESSES FOR KINETIC RESOLUTION OF BUTINOLESTERS

RELATED APPLICATIONS

This application is a national stage application under 35 U.S.C. 371 of PCT/EP2006/067056, filed Oct. 5, 2006, which is incorporated by reference in its entirety and claims benefit of European application 05109395.3, filed Oct. 10, 2005, which is incorporated by reference in its entirety.

FIELD OF THE INVENTION

This invention relates generally to enzymes having esterase activity and their use for processes for kinetic resolution of butinolesters.

BACKGROUND OF THE INVENTION

Directed evolution has emerged in the past decade as the most powerful method to improve biocatalysts.[1] For instance, the enantioselectivity of a D-hydantoinase could be reversed leading to a substantially improved process for the synthesis of optically pure L-amino acids.[2]

Reetz and Jaeger were able to increase the enantioselectivity of a lipase from *Pseudomonas aeruginosa* towards a chiral carboxylic acid (2-methyl decanoate) first from E=1.1 (wild-type) to E=11.[3] Using a combination of a broad range of molecular biology methods they were finally able to identify a variant with practically useful selectivity (E=51).[4] Similarly, we were able to increase the enantioselectivity of an esterase from *Ps. fluorescens* (PFE) towards 3-phenylbutyric acid from E=3.5 to E=12 by combining error-prone PCR with saturation mutagenesis.[5]

Successful directed evolution experiments strongly depend on several aspects: The identification of desired variants exhibiting an increased enantioselectivity strongly depends on the high-throughput screening method used, as the selectivity determined using a surrogate substrate (i.e. a p-nitrophenyl ester) can differ significantly from the true substrate (i.e. a methyl ester) which can lead to false positive variants. In addition, it is assumed that the random introduction of mutations does not significantly affect other properties of the biocatalyst and its production in the microbial host. Another aspect is the location of productive mutations. Directed evolution experiments often lead to variants, in which effective mutations were far from the active site region, although they affected substrate specificity or enantioselectivity and the question whether closer mutations are better has been already addressed in literature.[6]

The hydrolase-catalyzed resolution of the acetate of 1a is very challenging, as this secondary alcohol has only small differences in the size of its substituents. In accordance to the 'Kazlauskas rule'[7] it is converted by lipases or esterases only with low to modest E-values.

The (R)-alcohol can be used for the synthesis of (−)-akolactone A, a cyclotoxic butanolide[8], pancrastatin, an antitumor alkaloid[9], chiral cyclopropane-based ligands[10] and for the large-scale production of (R)-enzyl 4-hydroxyl-2-pentynoate.[11] Both pure enantiomers of 1a were employed in the preparation of enantio- and diastereomerically pure allylboronic ester by Johnson rearrangement, leading to enantiopure homoallyl alcohols.[12] Other examples include the synthesis of 3-bromo-pyrrolines from α-amino allenes[13], optically active bicyclic ligands used for the synthesis of HIV protease inhibitors[14] or key intermediates of $\alpha_v\beta_3$ antagonist (osteoporosis).[15] One example for an application of the (S)-alcohol is the preparation of chiral cyclic carbonates.[16]

Previously, we investigated >100 hydrolases for the kinetic resolution of 1b[17] and the best enzyme was the esterase from *Pseudomonas fluorescens* (PFE) recombinantly expressed in *E. coli*.[18] (SEQ ID NO:1). But detailed analysis of the reaction time course revealed, that the enantioselectivity considerably dropped during the hydrolysis of the acetate (Table 1) and complete conversion was observed leading to racemic alcohol 1a. A similar effect was described in a patent for an esterase from *Pseudomonas glumae*.[19] In the hydrolysis of the corresponding butyrate, the initial value was E ~30, but then dropped too at higher conversion making a high yield resolution impractical. Only Nakamura and coworkers reported acceptable enantioselectivity, but the small-scale resolution suffered considerably from the use of large amounts of lipase Amano AH and very long reaction times (2 d).[20] The alternative asymmetric enzymatic reduction of the ketone is hampered by the very low enantiomeric excess as shown for a NADPH-dependent alcohol dehydrogenase from *Lactobacillus brevis* affording the (R)-alcohol with 60% ee or a NADH-dependent *Candida parapsilosis* carbonyl reductase yielding the (S)-alcohol with 49% ee.[21] In addition, the 3-butyn-2-one is rather unstable with high risk for thermal decomposition restricting the large-scale reduction, even if a highly selective reductase is available.

OBJECT OF THE INVENTION

It was the object to provide highly effective hydrolases for the preparation of 3-butyn-2-ol in optically pure form, which do not have the flaws of the prior art enzymes.

DETAILED DESCRIPTION OF THE INVENTION

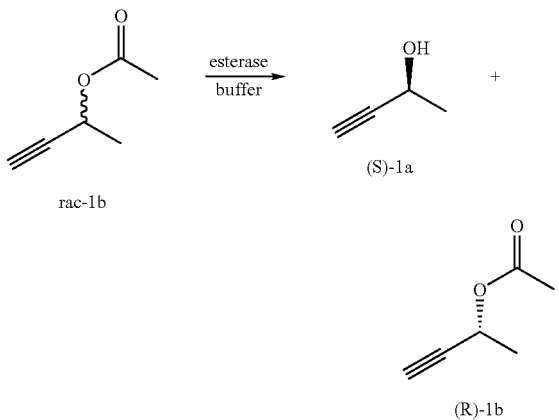

Scheme 1: Principle of esterase-catalyzed kinetic resolution.

To create an enantioselective variant to resolve 1b, epPCR libraries of PFE were created followed by high-throughput screening (HTS) using the 'acetic acid assay' previously developed in our laboratory.[22] Acetic acid released in the esterase-catalyzed hydrolysis of the acetate 1b is converted in an enzyme cascade reaction stoichiometrically into NADH quantified spectrophotometrically at 340 nm. As enantiopure (R)- and (S)-acetates were used in separate wells of a microtiter plate, the apparent enantioselectivity ($E_{app}$) of each esterase variant could be determined from these initial rate measurements. The E-values were then confirmed by kinetic resolution after shake flask production of positive esterase variants in small-scale experiments by GC analysis ($E_{true}$). After screening ~7,000 mutants, a PFE mutant was identified, which exhibited an $E_{true}$=89 at 54% conversion. Unfortunately, the reaction time was extremely long (>24 h) compared to only a few minutes required for similar conversion values using the PFE wildtype (data not shown).

Sequencing of this variant identified three point mutations (Ile76Val/Gly98Ala/Val175Ala). Surprisingly, cell fractionation and analysis of the pellet in SDS polyacrylamide gel electrophoresis showed that this triple mutant—in contrast to the wildtype—was produced as inclusion bodies (IB) at 37° C. and only a minor fraction of soluble protein was formed. This had a specific activity of only 0.0006 U $mg_{protein}^{-1}$ compared to 77 U $mg_{protein}^{-1}$ for the PFE wildtype using p-nitrophenyl acetate (pNPA) as assay substance. The inclusion body formation could be decreased by cultivation at 25° C. yielding a specific activity of 0.5026 U $mg_{protein}^{-1}$. Hydrolysis of 1b resulted in 44% conversion after 40 min, with a very high enantioselectivity (E>>100).

TABLE 1

Specific activities of PFE wildtype and variants towards pNPA, their E-values at 50% conversion and the enantioselectivity after prolonged reaction times ($E_{max}$).

| Label | PFE variant | Activity [U $mg_{protein}^{-1}$] lyophilisate | IB[a] | $E_{-50\%}$[b] | Time [min] | $E_{max}$[c] | Time [min] |
|---|---|---|---|---|---|---|---|
| WT | Wild-type | 77 | Š | 63 | 5 | 3 (96%) | 1440 |
| V2A | Ile76Val/Gly98Ala/Val175Ala | 0.006 | + | 89 | 5700 | 89 (54%) | 5700 |
| 2A | Gly98Ala/Val175Ala | 0.2 | + | >100[d] | 180 | >100 (40%) | 180 |
| VA₁ | Ile76Val/Gly98Ala | 0.6 | + | 80[e] | 10 | 80 (25%) | 10 |
| A₁ | Gly98Ala | 9 | + | >100 | 5 | 90 (57%) | 1500 |
| VEA₂ | Ile76Val/Asp99Glu/Val175Ala | 37 | Š | 92 | 420 | 92 (53%) | 420 |
| V | Ile76Val | 49 | Š | >100 | 1 | 16 (83%) | 1500 |
| VA₂ | Ile76Val/Val175Ala | 57 | Š | 96 | 20 | 96 (53%) | 20 |
| A₂ | Val175Ala | 67 | Š | >100 | 1 | 26 (74%) | 1500 |

[a]IB, inclusion body,
[b]calculated at 50% conversion,
[c]calculated at maximal conversion given in brackets (%),
[d]calculated at 40% conversion,
[e]calculated at 25% conversion,
WT = SEQ ID NO: 1

Four variants (VEA₂, V, VA₂ and A₂) lacking the Gly98Ala mutation exhibited specific activities similar to the wildtype without the formation of IB. It is noteworthy, that variant VEA₂ (Ile76Val/Asp99Glu/Val175Ala) formed no IB (compared to V2A) and had a specific activity similar to the WT. From this we concluded, that the Gly98Ala mutation (A₁) next to the catalytic triad is responsible for the formation of IB.

Next, the enantioselectivity of all variants was investigated by small-scale resolutions and we were pleased to find, that two mutants exhibited satisfying activity while the high enantioselectivity was maintained in the resolution of 1b: the double mutant VA₂ (Ile76Val/Val175Ala) with E=96 (53% conversion, 20 min) and VEA₂ (Ile76Val/Asp99Glu/Val175Ala) with E=92 (53% conversion, 7 h). Both variants have the same temperature stability and pH-optimum as PFE wildtype (data not shown).

Thus, we were able to create several esterase variants by directed evolution and sub-sequent site-directed mutagenesis, which show excellent enantioselectivity and kinetics in the resolution of the acetate of 3-butyn-2-ol yielding the (S)-enantiomer. Due to their high selectivity and activity, with this variant the (R)-enantiomer is also available from the remaining acetate.

A first embodiment of the invention is an isolated polypeptide with a sequence according to SEQ ID NO:1 with the proviso that at least one of the amino acids in position 76, 98, 99, 175 is different from the respective position in SEQ ID NO:1.

The isolated polypeptide according to the invention is a polypeptide which has in position 76 an amino acid selected from the group Phe, Leu, Met, Val, Ser, Pro, Thr, Ala, Tyr, His, Gln, Asn, Lys, Asp, Glu, Cys, Trp, Arg, Gly; and/or in position 98 an amino acid selected from the group Phe, Leu, Ile, Met, Val, Ser, Pro, Thr, Ala, Tyr, His, Gln, Asn, Lys, Asp, Glu, Cys, Trp, Arg; and/or in position 99 an amino acid selected from the group Phe, Leu, Ile, Met, Val, Ser, Pro, Thr, Ala, Tyr, His, Gln, Asn, Lys, Glu, Cys, Trp, Arg, Gly; and/or in position 175 an amino acid selected from the group Phe, Leu, Ile, Met, Ser, Pro, Thr, Ala, Tyr, His, Gln, Asn, Lys, Asp, Glu, Cys, Trp, Arg, Gly.

A preferred embodiment is a polypeptide having in position 76 of SEQ ID NO:1 a Val, Leu, Ala and/or in position 99 a Glu, Gln, Asn and/or in position 175 a Ala, Leu, Ile.

A more preferred embodiment is a polypeptide which has two or three of the above-mentioned positions altered compared to SEQ ID NO:1.

Preferably the polypeptide has a sequence according to SEQ ID NO:1 with the proviso that the amino acid in position 76 is Val and in position 175 is Ala and a sequence according to SEQ ID NO:1 with the proviso that the amino acid in position 76 is Val and in position 99 is Glu and in position 175 is Ala.

Some mutations of the amino acid in position 98 (Gly) result in polypeptides which were expressed in *E. coli* in the form of inclusion bodies, especially if Gly98 has been mutated to Ala98.

Another aspect of the invention is the use of the above-mentioned enzymes for kinetic resolution, especially for the kinetic resolution of racemic butinol esters.

A preferred embodiment is a process for preparing optically active 3-butyn-2-ol by hydrolysis of racemic 3-butyn-2-ol-ester in the presence of an polypeptide according to claim 1 to 6 and subsequent separation of the (S)-3-butyn-2-ol from the (R)-3-butyn-2-ol-ester.

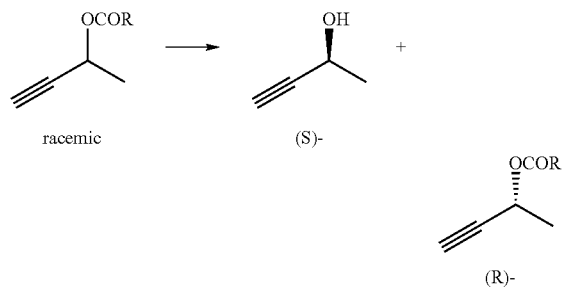

with R being H or $C_1$-$C_6$-Alkyl, preferred being Methyl.

The process according to the invention gives access to (S)-3-butyn-2-ol by separation of the end products. The separation can be achieved by methods known in the art such as distillation, extraction or chromatographic procedures.

If (R)-3-butyn-2-ol is the wanted product, the (R)-3-butyn-2-ol-ester of the above-mentioned process can hydrolyzed by treatment with a base such as KOH or NaOH or an alkalialcoholate such as NaOEt.

A preferred embodiment of the above-mentioned process is conducted in a buffered medium within a pH from 5 to 9, preferably from 6 to 8. As buffered medium phosphate is preferred.

Beside the creation of a biocatalyst useful for efficient kinetic resolution, this study also showed that a mutation close to the active site could have a substantial impact on protein folding. This aspect has not been described so far in literature and should be considered in protein engineering, especially using directed evolution methods. In addition, mutations near the active site must not lead to altered enantioselectivity and in this case rather remote mutations were shown to be most effective to create a highly enantioselective enzyme.

Furthermore, this is the first example for the successful creation of an esterase with substantially improved enantioselectivity towards secondary alcohols using methods of directed evolution.

EXPERIMENTS

General: All chemicals were purchased from Fluka (Buchs, Switzerland), Sigma (Steinheim, Germany) and Merck (Darmstadt, Germany), unless stated otherwise. Restriction enzymes, ligase, DNAseI and polymerases were obtained from Promega (Madison, Wis., USA) and New-England BioLabs GmbH (Beverly, Mass., USA). MWG-Biotech (Ebersberg, Germany) provided primers and performed sequencing.

Bacterial strains, plasmid, growth conditions and protein analysis: *E. coli* DH5α or JM109 were used as hosts for transformation of plasmid DNA. The strains were grown in LB liquid media or on LB agar plates supplemented with 100 μg ml$^{-1}$ ampicillin at 37° C.[25] The vector pJOE2792.1 with a rhamnose-inducible promoter was used for expression of PFE. Esterase production was induced upon addition of rhamnose (final concentration 0.2% v/v) and cultivation continued for 5 h. Cells were collected by centrifugation (15 min, 4° C., 3939 g) and washed twice with sodium phosphate buffer (10 mM, pH 7.4, 4° C.). Cells were disrupted by sonication on ice for 5 min at 50% pulse and centrifuged to separate soluble from insoluble fractions, the latter containing the inclusion bodies. The supernatant was lyophilized and stored at 4° C. Protein content was determined using Bradford reagent with bovine serum albumin as standard.

Esterase activity was determined spectrophotometrically by hydrolysis of p-nitrophenol acetate (pNPA, 10 mM in DMSO) in sodium phosphate buffer (10 mM, pH 7.4). p-Nitrophenol released was quantified at 410 nm ($\epsilon$=15*10$^3$ M$^{-1}$ cm$^{-1}$). One Unit (U) of activity was defined as the amount of enzyme releasing 1 μmol p-nitrophenol per min under assay conditions[25]. Proteins from soluble and insoluble fractions were also analyzed by a 12% separating and 4% stacking sodium dodecyl sulphate polyacrylamide gel.[25] After electrophoresis the gel was first activity-stained with α-naphthylacetate and Fast Red[18] followed by Coomassie brilliant blue staining.

Creation of epPCR Library: Plasmids, isolated using the QIAprep kit (Qiagen, Hilden, Germany), were used in the epPCR at a final concentration of 0.1 ng μl$^{-1}$. The reaction mixture was composed of 10 μl dNTP Mix (2 mM ATP, 2 mM GTP, 10 mM CTP, 10 mM TTP), 10 μl mutation buffer (70 mM MgCl$_2$; 500 mM KCl; 100 mM Tris pH 8; 0.1% (w/v) gelatine), 100 pmol of each primer (forward primer: GACTG-GTCGTAATGAACAATTC (SEQ ID NO: 2), reverse primer: AATGATGATGATGATGGCATC (SEQ ID NO: 3)), 1 μl Taq polymerase, 3 μl 10 mM MnCl$_2$ and plasmid DNA with a final volume of 100 μl. The reaction conditions were: 1) 95° C. 60 s, 2) 25 cycles: 95° C. 30 s, 50° C. 30 s, 72° C. 45 s, 3) 72° C. 150 s. The PCR products were purified with the QIAquick™. PCR Purification Kit, digested with BamHI and NdeI to generate cohesive ends, ligated in the empty vector pJOE2792.1 and transformed in competent *E. coli* cells prepared using the rubidium chloride method. Transformands were transferred by replica plating to an LB/Amp agar plate containing L-rhamnose to induce the esterase production and to analyze the activity towards x-naphthylacetate. Active clones showing a red color with Fast Red were transferred to microtiter plates (MTP) containing 200 μl LB/Amp in each well (master plate). The plates were incubated for 16 h at 37° C. and 50 rpm, glycerol or DMSO (end concentration 10%, v/v) were added and the MTP was stored at −80° C.

Enzyme production in microtiter plates with "Steady-State-Growth-Method": The master plates were duplicated by transferring the colonies with a 96 pin head into a new microtiter plate, containing 200 μl LB/Amp per well (production plate). These new plates were incubated for 24 h at 37° C. and 50 rpm, the cultures were then at the stationary growth phase. With a pipet robot (Miniprep 75, Tecan, Crailsheim, Germany) 100 μl culture were transferred from each well to a new MTP well containing 100 μl fresh LB/Amp, incubated for further 3 h to reach the exponential phase. Next, L-rhamnose was added to induce the esterase production for another 5 h. Cells were harvested by centrifugation (1750 g, 15 min, 4° C.) and the supernatants were discarded. 200 μl lysis buffer (300 mM NaCl, 50 mM Na$_2$HPO$_4$, pH 8) containing DNAseI (final concentration 1 U ml$^{-1}$) and lysozyme (final concentration 0.1% w/v) were added and cells were destroyed by one freeze-thaw-cycle. The supernatant containing the esterase was either lyophilized or directly stored at −20° C.

Synthesis of corresponding racemic and enantiopure acetates: Acetates were enzymatically synthesized in a transesterification reaction from 1 eq. rac-1a with 1.5 eq. vinyl acetate in 5 ml n-hexane, molecular sieves and 5 mg *Candida antarctica* lipase B (CAL-B, Novozym, Denmark), stirred at 37° C. overnight. Enzyme and molecular sieves were removed by centrifugation, solvent and excess vinyl acetate were evaporated. As CAL-B exhibited no enantioselectivity towards 1a, complete conversion to the racemic acetate was possible.

Screening with the acetic acid assay: The test kit for the determination of released acetic acid was from R-Biopharm GmbH (Darmstadt, Germany) and applied according to the manufactures protocol. To a 150 μl mixture of the test kit components, 20 μl of enzyme solution from the production plate and 20 μl substrate solution (7.5 mg ml$^{-1}$) of enantiopure (R)- or (S)-2-acetoxy-3-butyn (1b) were added. The increase of NADH was monitored at 340 nm using the "Fluostar Galaxy" or "Fluostar Optima" (BMG, Offenburg, Germany). Mixtures of test kit components with buffer or cell lysate of induced *E. coli* containing a vector without an esterase gene served as controls. The ratio of the initial rates thus determined for each enantiomer was defined as the apparent enantioselectivity ($E_{app}$)[17].

General method for esterase-catalyzed small-scale resolutions: To a stirred solution of substrate 1b (25 mM) in phosphate buffer (10 mM, pH 7.4) the esterase solution was added. The reaction mixture was stirred in a thermoshaker (Eppendorf, Hamburg, Germany) at 37° C. At different time points, 100 μl samples were taken and extracted two times with 100 μl dichloromethane. The combined organic layers were dried over anhydrous sodium sulphate and the organic solvent was removed under nitrogen. The samples were analyzed by gas chromatography (GC-14A Gaschromatograph, Shimadzu, Japan) using a chiral column Hydrodex™-β-3P (Heptakis-(2,6-di-O-methyl-3-O-pentyl-β-cyclodextrin) (25 m, 0.25 mm) with hydrogen as carrier gas. Enantioselectivity ($E_{true}$) and conversion were calculated according to Chen et al.[26]

QuikChange™: The QuikChange™ Site-Directed Mutagenesis Kit (Stratagene, La Jolla, USA) was used according to the manufacturers instructions with complementary primers: G229A exchange: 5'-CTTCGCCGACGAC ATCGCCCAGTTGATC-3' (SEQ ID NO: 4), C296G exchange: 5'-CATGGGCGGCGGCGATGTGGCCCG-3' (SEQ ID NO: 5) and C527T exchange: 5'-TCTCCCAAGGC GTGCAGACCCAGACC-3' (SEQ ID NO: 6); plasmids encoding for the triple mutant and the following reaction conditions: 1) 95° C. 45 s, 2) 20 cycles: 95° C. 45 s, 55° C. 60 s, 68° C. 10 min. The mutated plasmids were transformed into competent *E. coli* cells (4 μl reaction in 50 μl competent cells).

REFERENCES

[1] a) Arnold, F. H.; Volkov, A. A. *Curr. Opin. Chem. Biol.* 1999, 3, 54-59; b) Bornscheuer, U. T. *Angew. Chem.* 1998, 110, 3285-3288; *Angew. Chem., Int. Ed.* 1998, 37, 3105-3108; c) Jaeger, K.-E.; Eggert, T. *Curr. Opin. Biotechnol.* 2004, 15, 305-513; d) Reetz, M. T. *Proc. Natl. Acad. Sci. U.S.A.* 2004, 101, 5716-5722.

[2] May, O.; Nguyen, P. T.; Arnold, F. H. *Nat. Biotechnol.* 2000, 18, 317-320.

[3] Reetz, M. T.; Zonta, A.; Schimossek, K.; Liebeton, K.; Jaeger, K.-E. *Angew. Chem.* 1997, 109, 2961-2963; *Angew. Chem. Int. Ed. Engl.* 1997, 36, 2830-2832.

[4] a) Liebeton, K; Zonta, A.; Schimossek, K.; Nardini, M; Lang, D.; Dijkstra, B. W.; Reetz, M. T.; Jaeger, K.-E. *Chem. Biol.* 2000, 7, 709-718; b) Reetz, M. T. *Tetrahedron* 2002, 58, 6595-6602.

[5] Henke, E.; Bornscheuer, U. T. *Biol. Chem.* 1999, 380, 1029-1033.

[6] Morley, K. L.; Kazlauskas, R. J. *Trends Biotechnol.* 2005, 23, 231-237.

[7] Kazlauskas, R. J.; Weissfloch, A. N. E.; Rappaport, A. T.; Cuccia, L. A. *J. Org. Chem.* 1991, 56, 2656-2665.

[8] Gallagher, W. P.; Maleczka, R. E. J. *J. Org. Chem.* 2003, 68, 6775-6779.

[9] Ko, H.; Kim, E.; Park, J. E.; Kim, D.; Kim, S.; *J. Org. Chem.* 2004, 69, 112-121.

[10] Molander, G. A.; Burke, J. P.; Carroll, P. J. *J. Org. Chem.* 2004, 69, 8062-8069.

[11] Fu, X.; Yin, J.; Thiruvengadam, T. K.; McAllister, T. L.; Tann, C.-H.; Colon, C. *Org. Proc. Res. Devel.* 2002, 6, 308-310.

[12] Pietruszka, J.; Schöne, N. *Eur. J. Org. Chem.* 2004, 24, 5011-5019.

[13] Horváth, A.; Benner, J.; Baeckvall, J. E. *Eur. J. Org. Chem.* 2004, 15, 3240-3243.

[14] Yanada, R.; Koh, Y.; Nishimori, N.; Matsumura, A.; Obika, S.; Mitsuya, H.; Fujii, N.; Takemoto, Y. *J. Org. Chem.* 2004, 69, 2417-2422.

[15] Hartner, F. W.; Hsiao, Y.; Eng, K. K.; Rivera, N. R.; Palucki, M.; Tan, L.; Yasuda, N.; Hughes, D. L.; Weismann, S.; Zewge, D.; King, T.; Tschaen, D.; Voante, R. P. *J. Org. Chem.* 2004, 69, 8723-8730.

[16] Yoshida, M.; Ohsawa, Y.; Ihara, M. *J. Org. Chem.* 2004, 69, 1590-1597.

[17] Baumann, M.; Hauer, B. H.; Bornscheuer, U. T. *Tetrahedron: Asymmetry* 2000, 11, 4781-4790.

[18] Krebsfänger, N.; Zocher, F.; Altenbuchner, J.; Bornscheuer, U. T. *Enzyme Microb. Technol.* 1998, 22, 641-646.

[19] Hauer, B.; Friedrich, T.; Nübling, C.; Stürmer, R.; 2002. German patent application, DE10042892A1, 31 Aug. 2000.

[20] Nakamura, K.; Takenaka, K. *Tetrahedron: Asymmetry* 2002, 13, 415-422.

[21] Schubert, T.; Hummel, W.; Kula, M. R.; Müller, M. *Eur. J. Org. Chem.* 2001, 22, 4181-4187.

[22] Baumann, M.; Stürmer, R.; Bornscheuer, U. T. *Angew. Chem.* 2001, 113, 4329-4204; *Angew. Chem. Int. Ed.* 2001, 40, 4201-4204.

[23] Cheeseman, J. D.; Tocilj, A.; Park, S.; Schrag, J. D.; Kazlauskas, R. J. *Acta Crystallogr. D. Biol. Crystallogr.* 2004, 60, 1237-1243.

[24] Chou, P. Y. and Fasman, G. D., *Biochemistry* 1974, 13, 211-222

[25] Sambrook, J.; Fritsch, E. F.; Maniatis, T. *Molecular Cloning: a laboratory manual.*, Cold Spring Harbor Laboratory Press, Cold Spring Harbor, N.Y., 1989.

[26] Chen, C. S.; Fujimoto, Y.; Sih, C. J. *J. Am. Chem. Soc.* 1982, 104, 7294-7299.

The invention claimed is:

1. An isolated polypeptide comprising the amino acid sequence of SEQ ID NO:1, providing that an amino acid in position 175 is different from the corresponding amino acid in SEQ ID NO:1, and wherein the polypeptide has esterase activity.

2. The isolated polypeptide sequence of claim 1, wherein the amino acid in position 175 is Ala.

3. The isolated polypeptide sequence of claim 2, wherein the amino acid in position 76 is Val.

4. The isolated polypeptide sequence of claim 2, wherein the amino acid in position 99 is Glu.

5. The isolated polypeptide sequence of claim 1, wherein the amino acid in position 76 is Val, the amino acid in position 99 is Glu, and the amino acid in position 175 is Ala.

6. A process for preparing optically active 3-butyn-2-ol comprising hydrolyzing a racemic 3-butyn-2-ol-ester in the presence of the polypeptide of claim 1, followed by separating the resulting (S)-3-butyn-2-ol and the (R)-3-butyn-2-ol-ester.

7. The process of claim 6, wherein the racemic 3-butyn-2-ol-ester comprises die formula

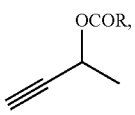

and wherein R is selected from the group consisting of H, methyl, and $C_1$-$C_6$ alkyl groups.

8. The process of claim 6, wherein the (R)-3-butyn-2-ol-ester is hydrolysed to (R)-3-butyn-2-ol by treatment with a base.

9. The process of claim 8, wherein the base is selected from the group consisting of KOH, NaOH, and an alkali alcoholate.

10. The process of claim 6, wherein the hydrolysis is conducted in a buffered medium within a pH range of 5 to 9.

11. The process of claim 6, wherein the hydrolysis is conducted in a buffered medium within a pH range of 6 to 8.

* * * * *

UNITED STATES PATENT AND TRADEMARK OFFICE
CERTIFICATE OF CORRECTION

PATENT NO. : 7,704,705 B2  Page 1 of 1
APPLICATION NO. : 12/083301
DATED : April 27, 2010
INVENTOR(S) : Uwe T. Bornscheuer et al.

It is certified that error appears in the above-identified patent and that said Letters Patent is hereby corrected as shown below:

In Claim 1, in column 11, line 44, "providing that an amino acid in position 175," should read -- providing that the amino acid in position 175, --.

Signed and Sealed this

Thirteenth Day of July, 2010

David J. Kappos
*Director of the United States Patent and Trademark Office*

SEQUENCE LISTING

<160> NUMBER OF SEQ ID NOS: 6

<210> SEQ ID NO 1
<211> LENGTH: 271
<212> TYPE: PRT
<213> ORGANISM: Pseudomonas fluorescens

<400> SEQUENCE: 1

Ser Thr Phe Val Ala Lys Asp Gly Thr Gln Ile Tyr Phe Lys Asp Trp
1               5                   10                  15

Gly Ser Gly Lys Pro Val Leu Phe Ser His Gly Trp Leu Leu Asp Ala
            20                  25                  30

Asp Met Trp Glu Tyr Gln Met Glu Tyr Leu Ser Ser Arg Gly Tyr Arg
        35                  40                  45

Thr Ile Ala Phe Asp Arg Arg Gly Phe Gly Arg Ser Asp Gln Pro Trp
    50                  55                  60

Thr Gly Asn Asp Tyr Asp Thr Phe Ala Asp Asp Ile Ala Gln Leu Ile
65                  70                  75                  80

Glu His Leu Asp Leu Lys Glu Val Thr Leu Val Gly Phe Ser Met Gly
                85                  90                  95

Gly Gly Asp Val Ala Arg Tyr Ile Ala Arg His Gly Ser Ala Arg Val
            100                 105                 110

Ala Gly Leu Val Leu Leu Gly Ala Val Thr Pro Leu Phe Gly Gln Lys
        115                 120                 125

Pro Asp Tyr Pro Gln Gly Val Pro Leu Asp Val Phe Ala Arg Phe Lys
    130                 135                 140

Thr Glu Leu Leu Lys Asp Arg Ala Gln Phe Ile Ser Asp Phe Asn Ala
145                 150                 155                 160

Pro Phe Tyr Gly Ile Asn Lys Gly Gln Val Val Ser Gln Gly Val Gln
                165                 170                 175

Thr Gln Thr Leu Gln Ile Ala Leu Leu Ala Ser Leu Lys Ala Thr Val
            180                 185                 190

Asp Cys Val Thr Ala Phe Ala Glu Thr Asp Phe Arg Pro Asp Met Ala
        195                 200                 205

Lys Ile Asp Val Pro Thr Leu Val Ile His Gly Asp Gly Asp Gln Ile
    210                 215                 220

Val Pro Phe Glu Thr Thr Gly Lys Val Ala Ala Glu Leu Ile Lys Gly
225                 230                 235                 240

Ala Glu Leu Lys Val Tyr Lys Asp Ala Pro His Gly Phe Ala Val Thr
                245                 250                 255

His Ala Gln Gln Leu Asn Glu Asp Leu Leu Ala Phe Leu Lys Arg
            260                 265                 270

<210> SEQ ID NO 2
<211> LENGTH: 22
<212> TYPE: DNA
<213> ORGANISM: Artificial Sequence
<220> FEATURE:
<223> OTHER INFORMATION: epPCR forward primer

<400> SEQUENCE: 2
gactggtcgt aatgaacaat tc                                              22

<210> SEQ ID NO 3
<211> LENGTH: 21
<212> TYPE: DNA

```
<213> ORGANISM: Artificial Sequence
<220> FEATURE:
<223> OTHER INFORMATION: epPCT reverse primer

<400> SEQUENCE: 3
aatgatgatg atgatggcat c                                              21

<210> SEQ ID NO 4
<211> LENGTH: 28
<212> TYPE: DNA
<213> ORGANISM: Artificial Sequence
<220> FEATURE:
<223> OTHER INFORMATION: Site-directed mutagenesis G229A exchange primer

<400> SEQUENCE: 4
cttcgccgac gacatcgccc agttgatc                                       28

<210> SEQ ID NO 5
<211> LENGTH: 24
<212> TYPE: DNA
<213> ORGANISM: Artificial Sequence
<220> FEATURE:
<223> OTHER INFORMATION: C296G exchange primer

<400> SEQUENCE: 5
catgggcggc ggcgatgtgg cccg                                           24

<210> SEQ ID NO 6
<211> LENGTH: 26
<212> TYPE: DNA
<213> ORGANISM: Artificial Sequence
<220> FEATURE:
<223> OTHER INFORMATION: C527T exchange primer

<400> SEQUENCE: 6
tctcccaagg cgtgcagacc cagacc                                         26
```